United States Patent [19]

Corstvet et al.

[11] Patent Number: 5,256,415
[45] Date of Patent: Oct. 26, 1993

[54] VACCINE AGAINST BOVINE RESPIRATORY DISEASE (PASTEURELLOSIS)

[75] Inventors: Richard E. Corstvet; Fred M. Enright, both of Baton Rouge, La.

[73] Assignee: Louisiana State University, Baton Rouge, La.

[21] Appl. No.: 919,706

[22] Filed: Jul. 24, 1992

Related U.S. Application Data

[63] Continuation of Ser. No. 325,866, Mar. 20, 1989, abandoned.

[51] Int. Cl.$^5$ .......................... A61K 39/02; C12N 1/36
[52] U.S. Cl. .................................... 424/92; 424/88; 424/93 R; 424/93 D; 435/243; 435/245
[58] Field of Search .............. 424/92, 88, 93 R, 93 D; 435/243, 245

[56] References Cited

U.S. PATENT DOCUMENTS 4,346,074  8/1982  Gilmour et al. ................... 424/92
4,957,739  9/1990  Berger et al. ..................... 424/92

OTHER PUBLICATIONS

Squire et al, *Infection and Immunity*, vol. 45, No. 3, pp. 667–673, 1984.

*Primary Examiner*—Michael G. Wityshyn
*Assistant Examiner*—Abdel A. Mohamed
*Attorney, Agent, or Firm*—William David Kiesel; Robert C. Tucker; Warner J. Delaune

[57] ABSTRACT

A vaccine against bovine respiratory disease is provided containing an attenuated strain of *Pasteurella haemolytica* isolated from an asymptomatic calf. The vaccine effectively triggers an immunological system response to whole cell, denuded, cytotoxin and capsular antigens.

6 Claims, 5 Drawing Sheets

VACCINE AGAINST BOVINE RESPIRATORY DISEASE (PASTEURELLOSIS)

This is a continuation of copending application Ser. No. 07/325,866 filed on Mar. 20, 1989, now abandoned.

BACKGROUND OF THE INVENTION

1. Field of the Invention

This invention relates to an attenuated mutant of *Pasteurella haemolytica*, biotype A, serotype 1 which is useful as a vaccine against bacterial respiratory disease in cattle.

2. Prior Art

A leading cause of bacterial respiratory disease in cattle is *P. haemolytica*. The disease is particularly contagious when animals are accumulated, such as prior to or during shipping. Monetary losses attributable to death, weight loss, lost milk production and treatment are estimated to be several hundred million dollars annually.

Various prior art vaccines have been developed for *P. haemolytica* with limited success. One of the difficulties has been finding a vaccine to produce antibody to all of the components of the virulent organism, especially to the cytotoxin and to certain cell membrane associated proteins. Furthermore, it is believed that none of the prior art viruses have an adverse effect on the potentiation of *P. haemolytica* by bovine viral diarrhea virus (BVDV). Bovine viral diarrhea virus has been found to potentiate pasteurellosis, although the exact mechanism is unknown.

Another shortcoming of the prior art viruses has been administration. One vaccine is given intradermally, an unusual and very inconvenient method for vaccinating cattle. Other prior art vaccines sometimes produce marked swelling and abscessation at the site of vaccination in greater than 5% of the animals.

SUMMARY OF THE INVENTION

Therefore, one object of this invention is to produce a *P. haemolytica* vaccine which is stable in the production of cell associated, cytotoxin, cell membrane and capsular immunogens.

Another object of this invention is to produce a vaccine which may be administered subcutaneously.

Still another object of this invention is to produce a vaccine which does not initiate an infection in the vaccinated animals and has a minimum of swelling at the site of inoculation.

Accordingly, a vaccine is provided comprising an attenuated mutant strain of *P. haemolytica*, biotype A, serotype 1 wherein said strain is selected from the group consisting of a strain of ATCC No. 53839 and a strain of ATCC No. 53840.

PREFERRED EMBODIMENT OF THE INVENTION

Figure 1:
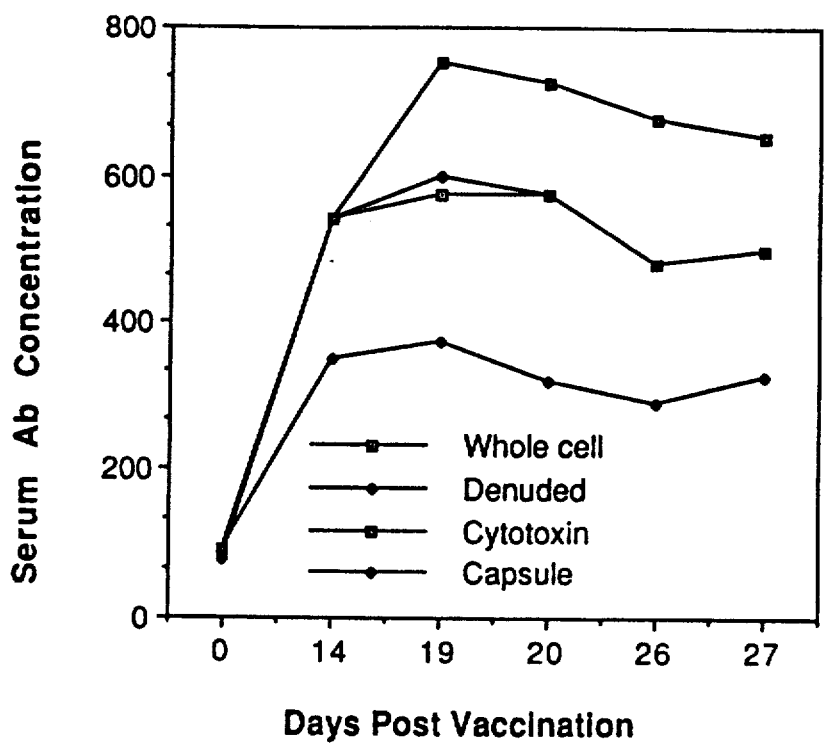
FIG. 1 is a graph of serum antibody concentration versus time for *P. haemolytica* associated immunogens following vaccination with ATCC #53840, inoculation with BVDV a with a field isolate.

Without limiting the scope of the invention, the preferred features of the invention are hereinafter described.

Preparation

A virulent field strain of *P. haemolytica*, biotype A, serotype 1, was isolated from the trachea of an asymptomatic, 400 pound feed-lot calf. The isolate was propagated on brain-heart infusion agar (YBP) with five percent (5%) citrated bovine blood, ten percent (10%) horse serum and one percent (1%) yeast at 35-37 C. in an atmosphere of 5-8% carbon dioxide. Concentrations in the agar are based upon weight/volume.

Monoclonal antibodies were prepared for capsular, cytotoxin and cell associated antigens using standard laboratory techniques.

The isolated field strain was passaged several times over a four year period to produce two variants, both of which are useful as vaccines. The two variants were produced as follows. Two passages of the field strain were made from lyophile on blood agar containing a brain-heart infusion base, 5% citrated bovine blood agar, 5-10% horse serum and 1% yeast extract. Incubation was at 37 in an atmosphere of 5-8% carbon dioxide. Approximately, $5 \times 10^9$ colony forming units were isolated from the blood agar and inoculated into the lung of a susceptible 250-400 pound calf. At 48 hours following the inoculation the calf was necropsied and the field strain was reisolated from the lung lesion. Lyophiles were made from this isolate. The above procedures were repeated about every six months.

These lyophilized cultures were reconstituted and grown on artificial medium. The smaller than normal colonies that were present in very low number were selected and propagated on various bacteriologic media. The media variations were a simple nutrient agar, a heart infusion agar and a brain-heart infusion agar. The horse serum varied from 0% to 15% and the 5% citrated bovine blood varied from 0-10%. It was determined that a consistently small to medium sized colony, that produced all the major antigens of the parent virulent strain and in like concentration, could be obtained using brain-heart infusion medium, 1% horse serum and 5% citrated bovine blood with incubation at 37 C. in an atmosphere of 5-8% $CO_2$. The colony size of the parent field isolate was stable at 2-3 mm in diameter on the above brain heart infusion agar. The mutants typically ranged from 1-3 mm in diameter with 1-2 mm being the usual size on the aforementioned agar.

These small colony mutants did not grow or grew sparsely at 25 C. and their colony size was related in part to the amount of horse serum in the medium. These mutants could be passaged onto artificial medium at least 50 times without loss of their ability to produce capsular antigens, cell membrane antigens, certain lipopolysaccharide-protein antigens and cytotoxin which is a secreted labile compound. The ability to produce these antigens was measured by laboratory tests using flurochromes, colloidal gold, electron microscopy, polyclonal antibody and monoclonal antibody. These antigens were produced in approximately the same concentration as in the parent strain.

Throughout the selection process, the mutants selected were consistent in ratio of small to medium colonies. Two mutants were finally selected as candidates for a vaccine and identified as variants ATCC #53839 and ATCC #53840. Variant #53840 produces a few small colonies while variant #53839 produces approximately 10 times more small colonies than variant ATCC #53840.

The variants were freeze dried in sterile skim milk at a concentration of 1,000,000,000 colony forming units per milliliter in an aliquot of 0.5 ml. They were stored at −6° C.

A lyophilized variant is reconstituted with 0.5 ml. sterile distilled water and the contents streaked for isolation on brain-heart infusion agar with 5% percent citrated bovine blood, 10% horse serum and 1% yeast extract and incubated at 37 C. in an atmosphere of 5-8% carbon dioxide for 18-24 hours. Several isolated colonies are picked and suspended in sterile distilled water and streaked onto the described medium with a cotton swab. The plates are incubated as described for the isolation from the lyophile. The growth is taken from the plates and suspended in 0.01M phosphate buffered saline made from pyrogen free water to an optical density of 0.25 measured at 650 nanometers wave length which, by a plate count method, is equal to 1,000,000,000 colony forming units per milliliter.

On Dec. 2, 1988 the variants were deposited with the American Type Culture Collection, Rockville, Md. and designated ATCC #53839 and ATCC #53840. The deposit has been accepted under the Budapest Treaty. All restrictions on the availability of progeny of the strains to the public will be irrevocably removed on the granting of a patent on which the strains are a subject.

These variants grow on MacConkey agar and are haemolytic on bovine blood agar. Their colony size and amount of growth varies directly with the concentration of horse serum in the medium and they are inactive on the usual laboratory biochemical media unless media for fastidious bacteria is used.

The serotype of the parent isolate and the variants was tested against polyvalent antiserum and monoclonal antibody prepared against various antigens of *P. haemolytica*, biotype A, serotype 1, and other *P. haemolytica* serotypes which were originally obtained from Dr. G. Frank of the National Veterinary Services Laboratory. All tests show that the parent isolate and the variants are *P. haemolytica*, biotype A, serotype 1.

Physiological Characteristics

The biochemical activity of each of the variants on a variety of substrates is represented below in Table 1.

| TEST | ATCC # 53839 | ATCC # 53840 |
|---|---|---|
| Ind | − | − |
| Tda | − | − |
| Dex | + | + |
| Cit | − | − |
| Esc | − | − |
| Onp | + | + |
| Mlo | − | − |
| Ure | − | − |
| Lys | − | − |
| Arg | − | − |
| Orn | − | − |
| H2S | − | − |
| Rha | − | − |
| Mlv | − | − |
| Man | + | + |
| Arb | + | + |
| Xyl | + | + |
| Suc | − | − |
| Mlt | + | + |
| Ace | − | − |
| Cet | + | + |

Antibiotic sensitivity was tested and produced in Table 2 below:

| ANTIBIODIC | ATCC 53839 | ATCC 53840 |
|---|---|---|
| Penicillin G P 10 | S | R |
| Augmentin AMC 30 | S | S |
| Chloramphenicol C 30 | S | S |
| Erythromycin E 15 | S | S |
| Oxacillin OX 1 | R | R |
| Clindamycin CC 2 | S | R |
| Tetracycline TE 30 | R | R |
| Nitrofurans FD 300 | S | S |
| Ampicillin AM 10 | S | R |
| Cephalothin CR 30 | S | S |
| Gentamicin GM 10 | S | S |
| Kanamycin K 30 | S | S |
| Sulfonamides SSS 300 | S | S |
| Carbenicillin CB 100 | S | S |
| Trimethoprim SXT 25 | S | S |
| Streptomycin | R | R |

S = Organism sensitive to antibiotic;
R = Resistant;
I = Intermediate

The aforementioned biochemical activity and antibiotic and sensitivity data was prepared using Johnston Laboratory Sceptor System, a minimum inhabitory concentration/identification computerized system (MIC/Id). Both ATCC #53839 and 53840 were found to have a 97.48% percent match to *P. haemolytica*. These strains have the unique characteristic of being very resistant to streptomycin. This resistance is a very stable and identifying characteristic to this strain and is believed not to be plasmid related.

The serologic data shows that both variants produce humoral antibody to all of the important immunogens, cytotoxin, capsular and cell associated immunogens. This antibody is of ample magnitude using 1 or 2 doses. Both variants prevent a septicemia in the vaccinate and neither one produces any mortality.

Variant ATCC #53840 also produces an immunity when given by an aerosal method whereby an aerosol was generated in a reservoir from which the calf breathed. Both variants produce satisfactory humoral response when adminstered via a subcutaneous implant (bacteria contained in a plastic device).

Neither variant, after subcutaneous administration, produces an elevated temperature, depression or signs of respiratory disease. Variant ATCC #53840 will produce a slight swelling at the site of inoculation in 5% of the calves. This swelling has not resulted in lameness, abscessation, or condemnation of the hide at slaughter. Variant ATCC #53839 did not produce any swelling at the site of inoculation.

Variant ATCC #53840 protected the lung even when a known potentiator of bovine pasteurellosis was present, bovine viral diarrhea virus (BVDV). Variant ATCC #53839 was not tested for this effect, but since it was derived from the same parent culture as ATCC #53840, it is expected to have a similar adverse affect on the viral induced potentiation of pasteurellosis. The lesion sizes support that lung resistance is produced with variant #ATCC 53840. The lesion data for ATCC #53839 does not support lung resistance, but only two animals have been tested. It is believed that given a less severe challenge, one which more closely approximates a field type exposure, variant ATCC #53839 will provide adequate lung resistance.

EXAMPLE 1

A vaccine was prepared by reconstituting a freeze dried culture of variant ATCC #53840 according to the previously described procedure. The suspension contained approximately 1,000,000,000 colony forming units per milliliter. The calves to be vaccinated varied from 250-500 pounds and were mixed breed, beef-type calves. Vaccination was performed with approximately 2.5 milliliters or 5 milliliters of the above described suspension given subcutaneously in the neck, just anterior to the shoulder.

Three calves were vaccinated with the suspension containing variant ATCC #53840 on Day 0. Fourteen days later the animals were inoculated with bovine viral diarrhea virus (BVDV). BVDV potentiates pasteurellosis in an unknown way but many scientist believe it may be through host immunosuppression. The animals were challenged 19 days after the vaccine with the original virulent isolate of P. haemolytica. The virulent isolate was introduced directly into the animal's lungs through a tube running down the animals trachea and into the lung cavity. Approximately 5.0 milliliters containing 1,000,000,000 colony forming units per milliliter were introduced.

Necropsy was performed 27 days after vaccination. The results were that one animal had a lung lesion approximately 2.5 by 3.5 centimeters and no lesions were found in the other two animals. The results are set out in Table 1 below.

TABLE 1

| | VACCINATED (1) - BVDV CHALLENGED | | | | |
|---|---|---|---|---|---|
| COW # | VAC #1 (Day) | INOC- BVDV (PVD) | CHAL- ISOLATE (PVD) | NECROPSY (PVD) | LESION (cm) |
| 1 | 0 | 14 | 19 | 27 | 2.5 × 3.5 |
| 2 | 0 | 14 | 19 | 27 | NL |
| 3 | 0 | 14 | 19 | 27 | NL |

PVD- Days post first vaccination
NL - No lesions

A comparative test was run with eight calves which were not vaccinated, only inoculated with BVDV followed by a challenge 5 days later with the same virulent isolate used above. A necropsy of the calves performed eight days after the challenge revealed relatively large lesions in most of the animals. The results are produced below in Table 2.

TABLE 2

| | NON-VACCINATED - BVDV CHALLENGED | | | | |
|---|---|---|---|---|---|
| COW # | VAC #1 (Day) | INOC- BVDV (PID) | CHAL- ISOLATE (PID) | NECROPSY (PID) | LESION (cm) |
| 4 | 0 | 0 | 5 | 13 | 5 × 6 |
| 5 | 0 | 0 | 5 | 13 | NL |
| 6 | 0 | 0 | 5 | 13 | 6 × 7 |
| 7 | 0 | 0 | 5 | 13 | 5 × 6 |
| 8 | 0 | 0 | 5 | 13 | Edema |
| 9 | 0 | 0 | 5 | 13 | 6 × 7 |
| 10 | 0 | 0 | 5 | 13 | 7 × 8 |
| 11 | 0 | 0 | 5 | 13 | 1.5 × 2 |

PID- Days post inoculation
NL - No lesions

Figure 2:
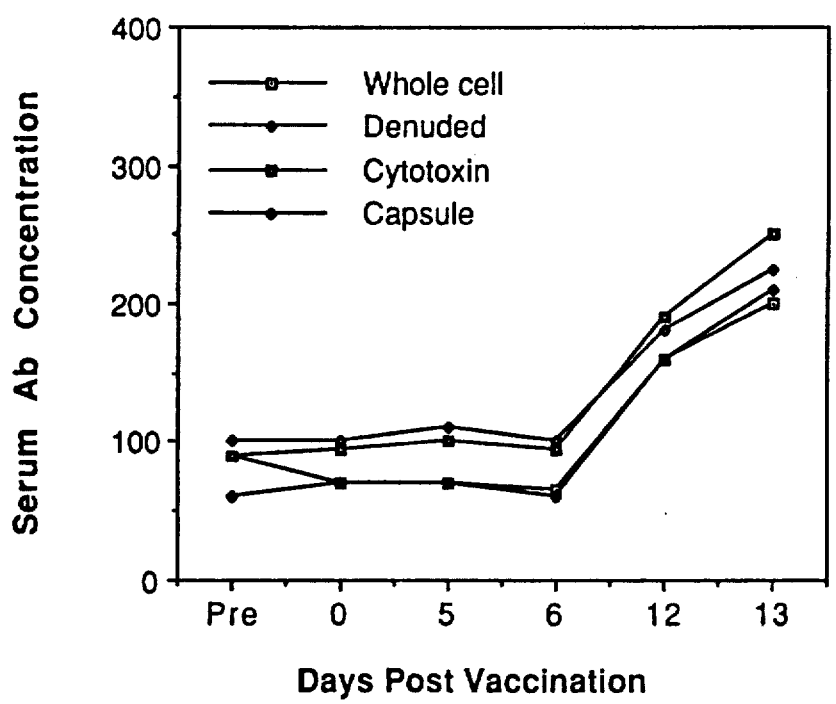
FIG. 2 is a graph of serum antibody concentration versus time for *P. haemolytica* associated immunogens following inoculation with BVDV and challenge with a field isolate.

Serum antibody concentration for whole cell, denuded (capsule removed), cytotoxin and capsular antigens versus time is shown in FIGS. 1 and 2 for vaccinated and non-vaccinated calves respectively. The data represents averages of all the animals in a particular test group. The data shows that the variant produces cytotoxin, capsular and cell associated immunogens corresponding to the parent isolate. The serologic data was obtained using a modified ELISA enzyme-linked immunosorbent assay) procedure using standardized concentrations of intact bacteria, bacteria from which capsule was removed (denuded), cytotoxin and capsule prepared from the parent isolate. Isolation of the capsular material and quantitative assay of capsular carbohydrate and protein are described in Gentry, Corstvet and Panciera, "Extraction of Capsular Material from Pasteurella haemolytica," Am. J. Vet. Res., Vol. 43, No. 11 (1982), and Smith, Lane and Gilkerson, "Quantitation of Glycosaminoglycan Hexosamine Using 3-Methyl-2 Benzothiazolone Hydrazone Hydrochloride", Analytical Biochemistry 98, pp. 478-480 (1979). Isolation and assay of the cytotoxin is described in Austin, Frank W., "Characterization and Application of Monoclonal Antibody in Bovine Neutrophil Reactivity to Pasteurella haemolytica Antigens", Ph.D. Thesis, Louisiana State University (1988).

In the ELISA procedure, plates are coated with 100 ul per well with antigen diluted in coating buffer. Suitable dilutions for whole cell, denuded, cytotoxin and capsular antigens are 1:400, 1:400, 1:300 and 1:200 respectively. The coating buffer is made up of 1.59 g $Na_2CO_3$, 2.93 g $NaHCO_3$, 0.2 g $NaN_3$ dissolved in one liter of distilled water which is filtered and sterilized. The plates are allowed to dry overnight at 37 C. in an incubator.

On the following day the coated plates are removed from the incubator and washed three times with a wash solution containing 58 g NaCl and 0.1% Tween 20 per one liter distilled water. Each wash consists of filling all the wells of the plate, allowing it to sit for five minutes then draining by suction. Following the three washes, the plates are inverted to drain.

The test bovine serum is diluted 1:800 in serum diluent containing 58 g NaCl, 0.1% Triton X-100 and EPBS added to one liter. EPBS is made from combining solution A containing 8 grams NaCl, 0.2 grams KCl, and 1.358 grams $Na_2HPO_4$ in one liter of distilled water with solution B containing 8 g NaCl, 0.2 g KCl, 1.302 g KH$_2$PO$_4$ dissolved in one liter of distilled water until a pH of 7.4 is reached, approximately 500 ml solution B to 2000 ml solution A. The EPBS diluent is filtered and sterilized before being combined to make the serum diluent.

Next 100 ul per well of diluted bovine serum is added to the washed ELISA plates. Prior to adding the diluted bovine serum to the ELISA plates, the serum may be set up in transfer plates to allow a 12 channel pipetter to be used. The ELISA plates and bovine serum are incubated for 90 minutes at room temperature in a humid chamber. Following incubation the plates are drained and washed three times using the procedure and wash solution described above.

After the plates have been drained, conjugate (Kirkegaard & Perry Laboratories #041206, goat anti-bovine IgG H & L chain peroxidase conjugate) which has been diluted 1:500 in a conjugate diluent containing EPBS plus 0.5% goat serum, is added in the amount of 100 ul/well. The plates are then incubated for 90 minutes at room temperature in a humid chamber, drained and washed three times using the wash solution and procedure described above.

Last, 100 ul/well of ABTS substrate (KPL peroxidase substrate system catalog no. 506201, mixed as directed) is added to one plate at a time allowing an approximate 5 minute interval between plates to allow time to read and record each plate. The optimum wave length to read results lies between 398 and 415 nm.

Figure 9:
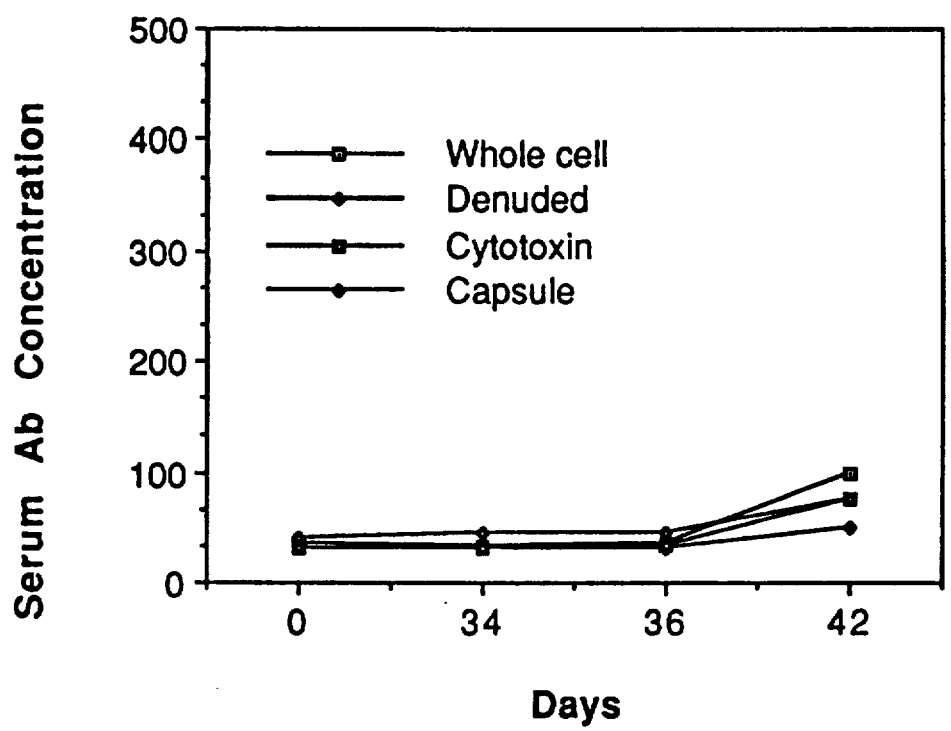
FIG. 9 is a graph of serum antibody concentration versus time in the unvaccinated, unchallenged controls.

FIG. 9 shows a graph of serum antibody concentration versus time for a non-vaccinated control calf.

EXAMPLE 2

A vaccine containing a suspension of variant ATCC #53840 was prepared as in Example 1. The vaccine was administered to 4 calves on Day 0 and then again seven days later. The animals were inoculated with BVDV 21 days following the first vaccination and challenged 26 days after the first vaccination. Necropsy performed eight days after the challenge revealed small lesions in two of the calves and no lesions in the other two. The results are summarized in Table 3.

TABLE 3

| | VACCINATED (2) - BVDV CHALLENGED | | | | | |
|---|---|---|---|---|---|---|
| COW # | VAC #1 (Day) | VAC #2 (PVD) | INOC-BVDV (PVD) | CHAL-ISOLATE (PVD) | NECROPSY (PVD) | LESION (cm) |
| 12 | 0 | 7 | 21 | 26 | 34 | 2 × 3 |
| 13 | 0 | 7 | 21 | 26 | 34 | 2 × 3 |
| 14 | 0 | 7 | 21 | 26 | 34 | NL |
| 15 | 0 | 7 | 21 | 26 | 34 | NL |

PVD - Days post first vaccination
NL - No lesions

A comparative test of a group of 4 cows was run by vaccinating them with Dulbecco's phosphate buffered saline (DuPBS) on Day 0 and again seven days thereafter. Likewise, the animals were inoculated with BVDV, challenged with the isolate and killed at 21 days, 26 days and 34 days respectively, following the first saline vaccination. The results produced in Table 4 below demonstrate relatively large lesions in most of the animals.

TABLE 4

| | DuPBS VACCINATED - BVDV CHALLENGED | | | | | |
|---|---|---|---|---|---|---|
| COW # | VAC #1 SALINE (Day) | VAC #2 SALINE (PVD) | INOC-BVDV (PVD) | CHAL ISOLATE (PVD) | NECROPSY (PVD) | LESION (cm) |
| 16 | 0 | 7 | 21 | 26 | 34 | Pleura |
| 17 | 0 | 7 | 21 | 26 | 34 | 8 × 10 |
| 18 | 0 | 7 | 21 | 26 | 34 | 8 × 10 |
| 19 | 0 | 7 | 21 | 26 | 34 | 5 × 7 |

PVD - Days post first vaccination

Figure 3:
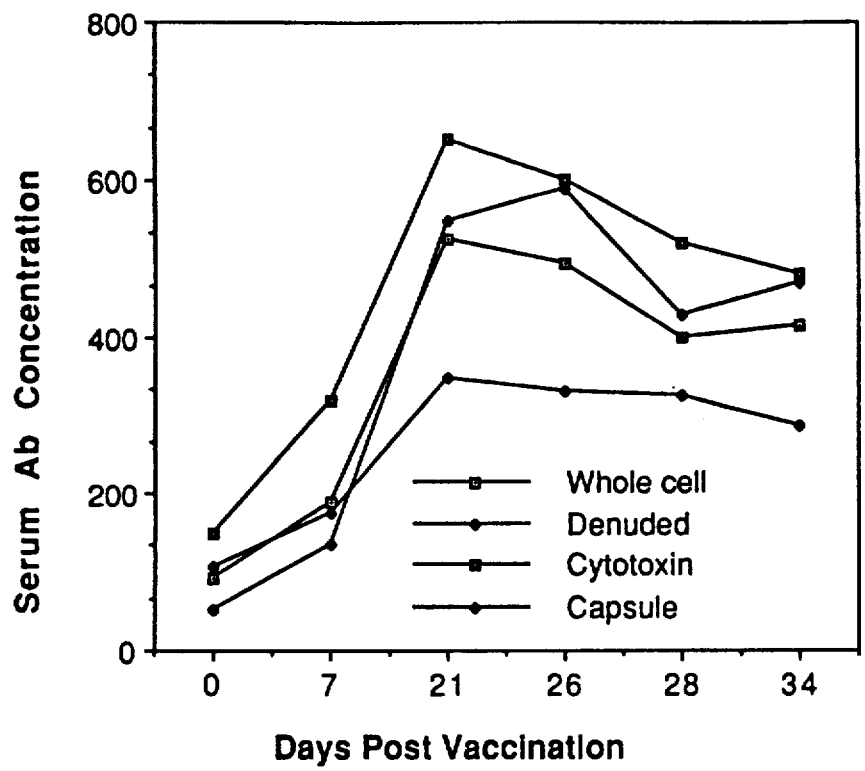
FIG. 3 is a graph of serum antibody concentration versus time for *P. haemolytica* associated immunogens following two vaccinations with ATCC #53840, inoculation with BVDV and challenge with a field isolate.
Figure 4:
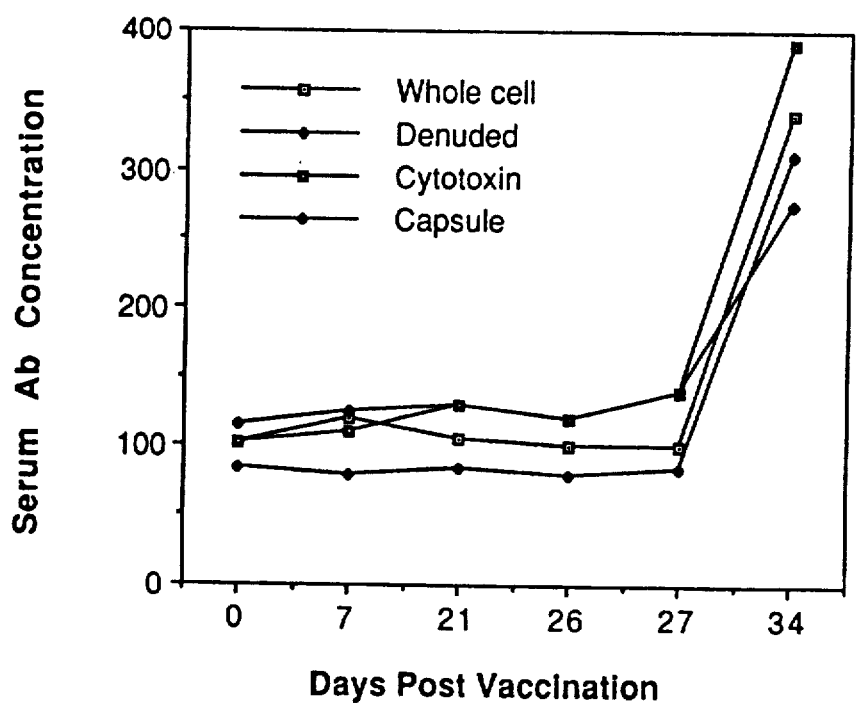
FIG. 4 is a graph of serum antibody concentration versus time for *P. haemolytica* associated immunogens following two vaccinations with saline, inoculation with BVDV and challenge with a field isolate.

Graphs of serum antibody concentration versus time for both the variant ATCC #53840 vaccinated and DuPBS vaccinated animals for the important immunogens are shown in FIGS. 3 and 4 respectively.

Figure 5:
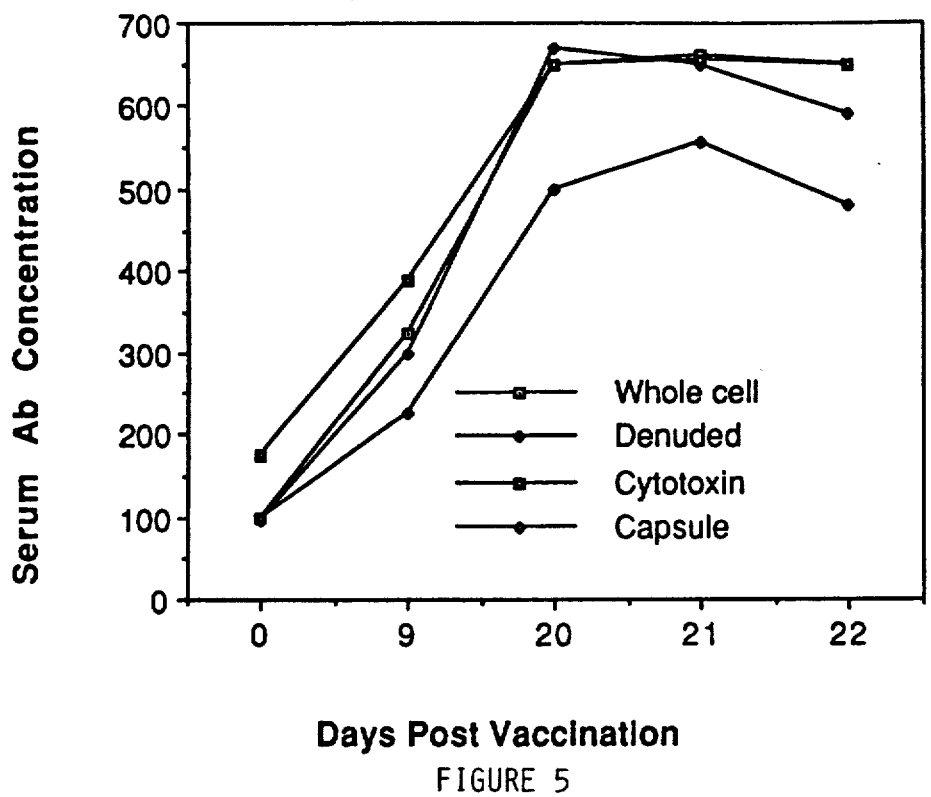
FIG. 5 is a graph of serum antibody concentration versus time for *P. haemolytica* associated immunogens following two vaccinations with ATCC #53840, inoculation with saline and challenge with a field isolate.

An additional experiment was run with 4 calves which were vaccinated twice and then challenged with the isolate but did not involve inoculation with BVDV prior to the challenge. The animals were vaccinated at Day 0 and Day 6 followed by inoculation with saline solution at Day 9. The animals were challenged with the isolate at 20 days following the first vaccination. A plot of serum antibody concentration versus time shown in FIG. 5 shows that variant ATCC #53840 produces humoral antibody to all of the important bacterial immunogens.

EXAMPLE 3

Figure 6:
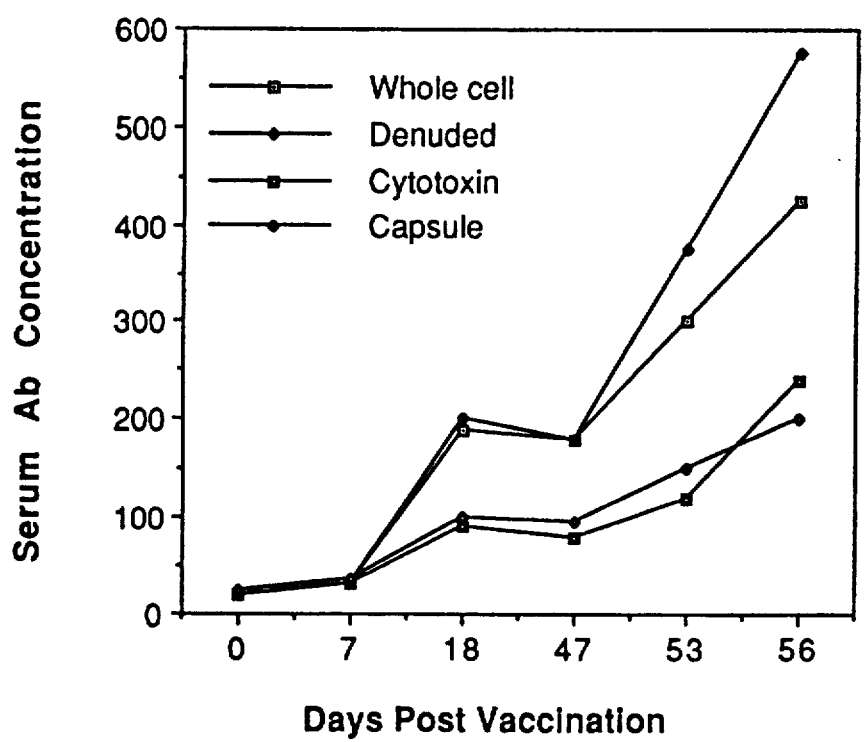
FIG. 6 is a graph of serum antibody concentration versus time for *P. haemolytica* associated immunogens following two vaccinations with ATCC #53839 and challenge with a field isolate.

A freeze dried culture of variant ATCC #53839 was reconstituted and a vaccine was prepared as described in Example 1. In the first experiment, the vaccine was given to two animals at Day 0 and Day 7 and the animals were challenged on the 47 day. A graph of serum antibody concentration versus time is shown in FIG. 6.

Figure 7:
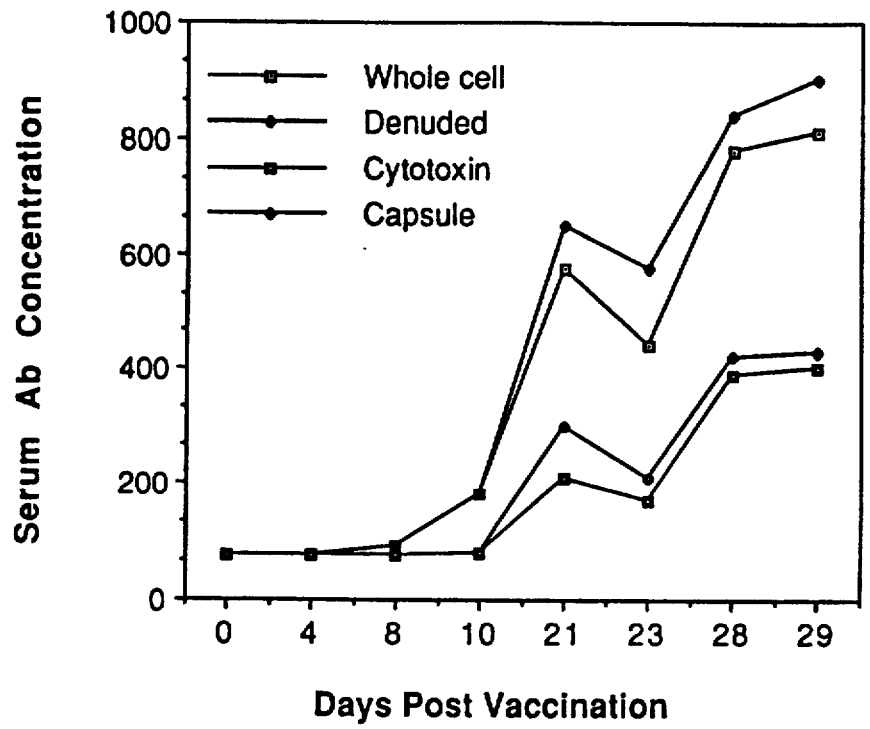
FIG. 7 is a graph of serum antibody concentration versus time for *P. haemolytica* associated immunogens following a vaccination with ATCC #53839 and a challenge with a field isolate.
Figure 8:
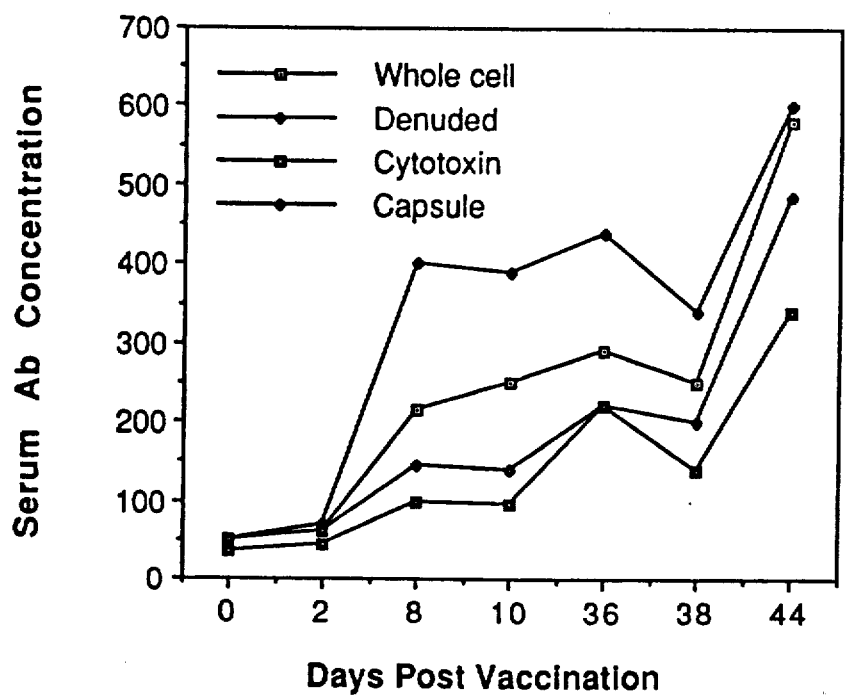
FIG. 8 is a graph of serum antibody concentration versus time for *P. haemolytica* associated immunogens following a vaccination with ATCC #53839 and a challenge with a field isolate.

FIGS. 7 and 8 show graphs of serum antibody concentration on experiments done with one animal each. The animals were vaccinated once and challenged at 21 days and 36 days respectively. The data for variant ATCC #53839 shows production of humoral antibody to all of the important immunogens.

There are, of course, many obvious alternate embodiments and modifications to this invention which are intended to be included within the scope of this invention as defined by the following claims. As used herein, the term derived culture encompasses any culture, including mutations, whether natural or artificially induced, of ATCC #53839 or ATCC #53840 which still exhibits those characteristics of the deposited cultures which are essential for carrying out the invention herein.

What I claim is:

1. A vaccine against bovine respiratory disease comprising:

(a) an effective immunological system triggering concentration of live organisms having capsular antigens selected from the group consisting of a strain of ATCC #53839 and a strain of ATCC #53840; and (b) a carrier.

2. A vaccine composition comprising an attenuated strain of *Pasteurella haemolytica* having the identifying characteristics of ATCC #53839.

3. A vaccine according to claim 2 further comprising a pharmaceutically acceptable diluent.

4. A vaccine composition comprising an attenuated strain of *Pasteurella haemolytica* having the identifying characteristics of ATCC #53840.

5. A vaccine according to claim 4 further comprising a pharmaceutically acceptable diluent.

6. A process for vaccinating an animal against *Pasteurella haemolytica*, biotype A, serotype 1 comprising the step of presenting an effective immunological system triggering culture of live organisms having capsulator antigens of *Pasteurella haemolytica*, biotype A, serotype 1, to said animal's immunological system wherein said culture is derived from the group consisting of a strain of ATCC #53839 and a strain of ATCC #53840.

* * * * *

UNITED STATES PATENT AND TRADEMARK OFFICE
CERTIFICATE OF CORRECTION

PATENT NO. : 5,256,415
DATED : October 26, 1993
INVENTOR(S) : Richard E. Corstvet; Fred M. Enright; and J. Raymond McClure It is certified that error appears in the above-identified patent and that said Letters Patent is hereby corrected as shown below:

On title page, item [75] should read —Richard E.

Corstvet; Fred M. Enright; and J. Raymond McClure, all of Baton Rouge, La.--

Signed and Sealed this

Sixteenth Day of May, 1995

Attest:

Attesting Officer

BRUCE LEHMAN

*Commissioner of Patents and Trademarks*